(12) United States Patent
Roshdy

(10) Patent No.: US 7,055,694 B2
(45) Date of Patent: *Jun. 6, 2006

(54) BLISTER TRAY WITH A PACKAGE FOR A SMALL DEVICE

(75) Inventor: Constance E. Roshdy, Mount Bethel, PA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/828,791

(22) Filed: Apr. 21, 2004

(65) Prior Publication Data

US 2004/0195145 A1   Oct. 7, 2004

Related U.S. Application Data

(62) Division of application No. 10/039,173, filed on Dec. 31, 2001, now Pat. No. 6,814,236.

(51) Int. Cl.
*B65D 69/00* (2006.01)

(52) U.S. Cl. ............. 206/571; 206/459.5; 206/366; 206/438

(58) Field of Classification Search ........ 206/363–370, 206/438, 485 X, 486 X, 476, 372, 373, 570, 206/571

See application file for complete search history.

(56) References Cited

U.S. PATENT DOCUMENTS

| | | | |
|---|---|---|---|
| 1,367,600 A | 2/1921 | Hirsch | |
| 1,446,741 A | 2/1923 | Faber | |
| 2,025,522 A | 12/1935 | Myers | |
| 2,224,027 A | 12/1940 | Tate | |
| 2,944,665 A | 7/1960 | Obeck | |
| 2,974,782 A | 3/1961 | Walters | |
| 2,990,059 A * | 6/1961 | Hitt | 206/365 |
| 3,058,584 A | 10/1962 | Marshall | |
| 3,153,531 A | 10/1964 | Cook | |
| 3,248,017 A | 4/1966 | Allen | |
| 3,497,982 A | 3/1970 | Schulz | |
| 3,698,551 A | 10/1972 | Tomlinson | |
| 3,927,762 A | 12/1975 | Zdarsky et al. | |
| 3,951,261 A | 4/1976 | Mandel et al. | |
| 3,951,263 A | 4/1976 | Vale | |
| 4,023,678 A | 5/1977 | Fiedler | |
| 4,091,927 A | 5/1978 | Lunsford | |
| 4,412,617 A | 11/1983 | Cerwin | |
| 4,424,898 A | 1/1984 | Thyen et al. | |
| 4,482,053 A | 11/1984 | Alpern et al. | |
| 4,619,364 A | 10/1986 | Czopor, Jr. | |
| 4,736,850 A | 4/1988 | Bowman et al. | |
| 4,915,233 A | 4/1990 | Smith | |
| 4,935,011 A * | 6/1990 | Hogan | 604/177 |
| 4,976,354 A * | 12/1990 | Levy | 206/456 |
| 5,024,323 A | 6/1991 | Bolton | |
| 5,099,994 A | 3/1992 | Kalinski et al. | |
| 5,199,567 A | 4/1993 | Discko, Jr. | |
| 5,322,163 A | 6/1994 | Foos | |
| 5,323,907 A | 6/1994 | Kalvelage | |

(Continued)

*Primary Examiner*—Jila M. Mohandesi

(57) ABSTRACT

A kit is disclosed which includes a blister tray and a package for a small device insertable within the blister tray. The blister tray has at least one medical device contained therein. The package includes a pair of end flaps engageable with the medical device such that the medical device, contained within the blister tray, inhibits the removal of the package from the blister tray. A plurality of openings is provided in the package and cooperates with each other to form a receptacle for a medical device, such as a vessel inverter.

5 Claims, 7 Drawing Sheets

U.S. PATENT DOCUMENTS

| | | |
|---|---|---|
| 5,351,822 A | 10/1994 | Sinn |
| 5,353,922 A | 10/1994 | Sinn |
| 5,358,116 A | 10/1994 | Brintazzoli |
| 5,361,907 A | 11/1994 | Mohrhauser |
| 5,375,717 A | 12/1994 | Roshdy |
| 5,379,895 A | 1/1995 | Foslien |
| 5,386,908 A | 2/1995 | Sinn |
| 5,392,919 A | 2/1995 | Passamoni |
| 5,477,964 A | 12/1995 | Hart |
| 5,485,917 A | 1/1996 | Early |
| 5,485,919 A | 1/1996 | Samberg et al. |
| 5,501,341 A * | 3/1996 | Van Es ................ 206/364 |
| 5,544,755 A | 8/1996 | Paumen et al. |
| 5,575,382 A | 11/1996 | Sobel et al. |
| 5,577,606 A | 11/1996 | Schwentuckowski et al. |
| RE35,445 E | 2/1997 | Pora |
| 5,617,952 A | 4/1997 | Kranendonk |
| 5,699,909 A | 12/1997 | Foster |
| 5,704,469 A | 1/1998 | Daniele et al. |
| 5,788,062 A | 8/1998 | Cerwin et al. |
| 5,788,063 A | 8/1998 | Van Ness |
| 5,791,470 A * | 8/1998 | Usui ................ 206/362.4 |
| 5,915,564 A * | 6/1999 | Hsi-Chang ................ 206/784 |
| 5,928,611 A | 7/1999 | Leung |
| 5,947,284 A | 9/1999 | Foster |
| 6,047,826 A | 4/2000 | Kalinski et al. |
| 6,170,663 B1 | 1/2001 | Glassman |
| 6,346,109 B1 | 2/2002 | Fucci et al. |
| 6,394,269 B1 | 5/2002 | Rudnick et al. |
| 6,412,639 B1 | 7/2002 | Hickey |
| 6,425,704 B1 | 7/2002 | Voiers et al. |
| 6,439,789 B1 | 8/2002 | Ballance et al. |
| 6,458,095 B1 | 10/2002 | Wirt et al. |
| 6,691,868 B1 | 2/2004 | Roshdy |
| 6,793,078 B1 | 9/2004 | Roshdy |
| 2001/0031170 A1 | 10/2001 | Voiers et al. |
| 2002/0108875 A1 | 8/2002 | Feinberg et al. |
| 2002/0176732 A1 | 11/2002 | Quintero et al. |
| 2003/0121821 A1 | 7/2003 | Roshdy |

* cited by examiner

BLISTER TRAY WITH A PACKAGE FOR A SMALL DEVICE

CROSS REFERENCE TO RELATED APPLICATION

This application is a divisional of U.S. patent application Ser. No. 10/039,173, filed Dec. 31, 2001, now U.S. Pat. No. 6,814,236, the disclosure of which is incorporated herein by reference in its entirety.

FIELD OF THE INVENTION

The present invention relates to a blister tray that contains a package for a small device, and more specifically to a blister tray that contains a package for a small device for use in a kit containing medical devices. As used herein, the term "medical device" includes a medical or surgical device.

BACKGROUND OF THE INVENTION

Medical devices are typically packaged in kits containing one or more medical devices. Conventionally, a kit contains a tray which includes recesses sized and shaped to receive medical devices. After a tray is formed with the appropriate recesses for the medical devices, it is very difficult and expensive to add or to make changes to the formed tray such that an additional small device can be incorporated therein.

Accordingly, there is a need to provide a package that can hold a small device to be incorporated into a formed tray, that can be easily assembled, and that can be easily arranged into the formed tray.

SUMMARY OF THE INVENTION

In accordance with the present invention, a kit is disclosed which includes a blister tray having a first medical device contained therein and a package for a small device sized and shaped to be insertable within the blister tray. The package for a small device includes a portion engageable with the first medical device such that the first medical device inhibits the removal of the package from the blister tray.

In one embodiment, the package is made from a planar sheet. The package includes a first foldable panel that has first and second fold lines. The second fold line is positioned on one side of the first fold line. The package further includes a main section and a center section. The main section is positioned on an opposite side of the first fold line, while the center section is positioned between the first and second fold lines. The first main section has a first slit that forms a retaining portion moveable such that the retaining portion extends outwardly from the main section. When the retaining portion extends outwardly from the main section, a first opening is formed in the first panel. The first main section also has a second slit that forms a first base moveable such that the first base extends outwardly from one side of the first panel. When the first base extends outwardly from one side of the first panel, a second opening is formed in the first panel. The center section has a third slit that forms a second base moveable such that the second base extends outwardly from one side of the first panel. When the second base extends outwardly from one side of the first panel, a third opening is formed in the first panel. The first and second openings align with each other when the first panel is folded about the first fold line such that the first base is adjacent to the second base. The first, second, and third openings cooperate with each other, when the first and second openings are aligned with each other, to form a receptacle for a medical device.

Other features and aspects of the present invention will become more fully apparent from the following detailed description of the preferred embodiments, the appended claims and the accompanying drawings.

BRIEF DESCRIPTION OF THE DRAWINGS

For a more complete understanding of the present invention, reference is made to the following detailed description of the exemplary embodiments considered in conjunction with the accompanying drawings, in which.

DETAILED DESCRIPTION OF THE EXEMPLARY EMBODIMENTS

Figure 1:
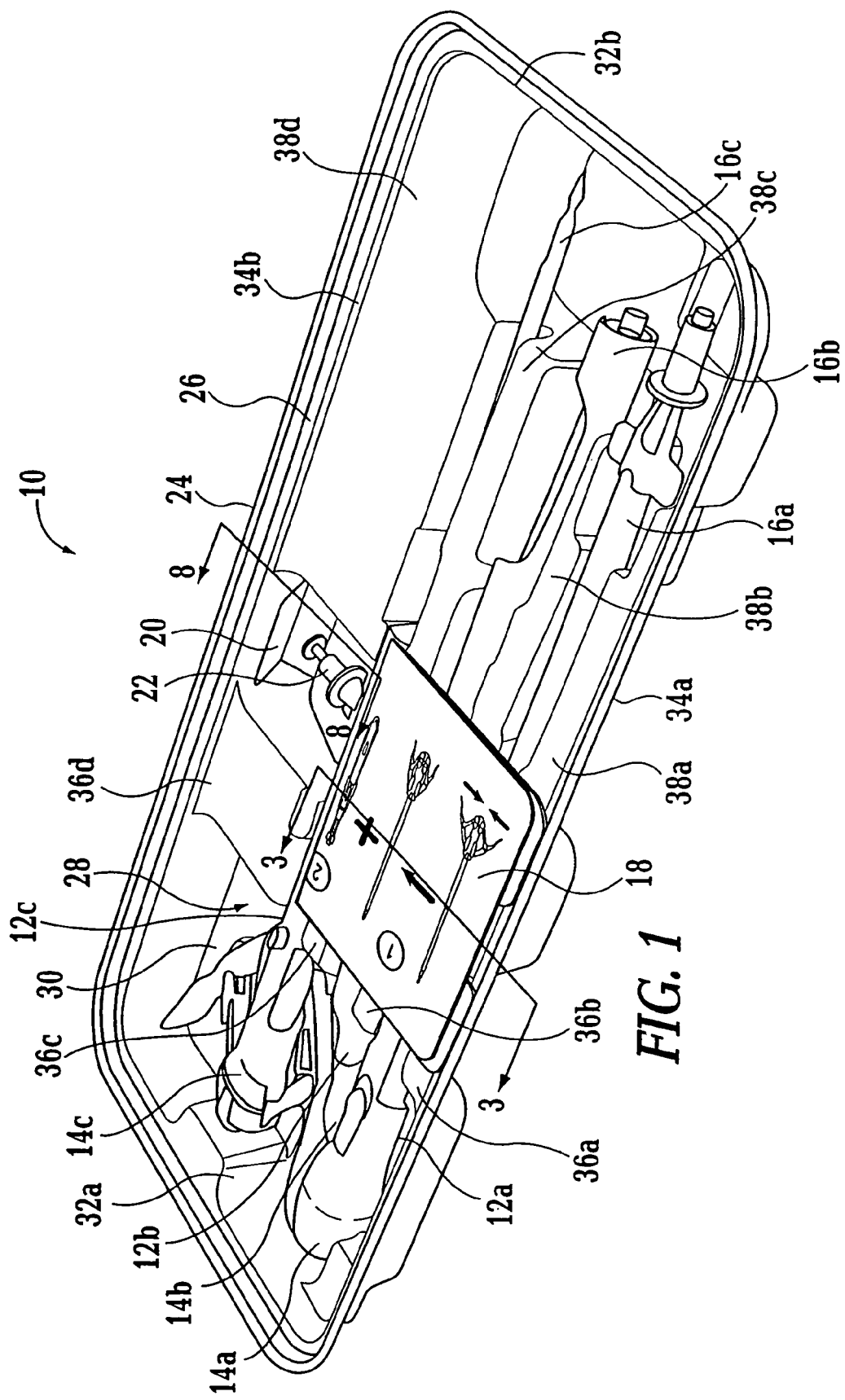
FIG. 1 is a perspective view of a blister tray, shown with a blister card and a device package, all of which are constructed in accordance with an exemplary embodiment of the present invention.

FIG. 1 shows a blister tray 10 sized and shaped to receive a plurality of medical devices 12a–c, each of which includes a handle 14a–c, respectively, and an elongated shaft 16a–c extending from the handle 14a–c. Further, the blister tray 10 is sized and shaped to receive a blister card 18 and a package 20 which contains a vessel inverter 22.

Referring to FIG. 1, the blister tray 10 includes an outer peripheral rim 24, an inner peripheral ledge 26, and an inner compartment 28 having a base 30. The blister tray 10 also has two lateral sides 32a–b and two longitudinal sides 34a–b, each of which extends upwardly from the base 30. As illustrated in FIG. 1, the medical devices 12a–c extend in parallel fashion with respect to each other and to the longitudinal sides 34a–b of the blister tray 10.

Still referring to FIG. 1, two sets of outwardly extending prominences 36a–d, 38a–d divide the blister tray 10 into a plurality of compartments, each of which is defined by recesses 40a–c (see FIG. 4), respectively, and each of which extend laterally between the longitudinal sides 34a–b of the blister tray 10. A groove 42a (see FIG. 4) is formed between an adjacent pair of prominences 36a–b, while a groove 42b (see FIG. 4) is formed between an adjacent pair of prominences 36b–c. Also, a groove 42c (see FIG. 4) is formed between an adjacent pair of prominences 36c–d. A groove 44a (see FIG. 4) is formed between an adjacent pair of prominences 38a–b, while a groove 44b (see FIG. 4) is formed between an adjacent pair of prominences 38b–c. Also, a groove 44c (see FIG. 4) is formed between an adjacent pair of prominences 38c–d. The grooves 42a–c, 44a–c formed between each adjacent prominence 36a–d, 38a–d, respectively, are aligned longitudinally such that the groove 42a is aligned with the groove 44a, the groove 42b is aligned with the groove 44b, and the groove 42c is aligned with the groove 44c. In this manner, the grooves 42a, 44a cooperate to receive two portions of the elongated shaft 16a of the medical device 12a, the grooves 42b, 44b cooperate to receive two portions of the elongated shaft 16b of the medical device 12b, while the grooves 42c, 44c cooperate to receive two portions of the elongated shaft 16c of the medical device 12c.

Although the blister card 18 and the device package 20 can be inserted into other blister trays, the blister card 18 and the device package 20 are described for use within the blister tray 10. It should be understood, however, that the foregoing description of the blister tray 10 is only meant to be illustrative of one type of blister tray and is not meant to limit the scope of the present invention.

Figure 2:
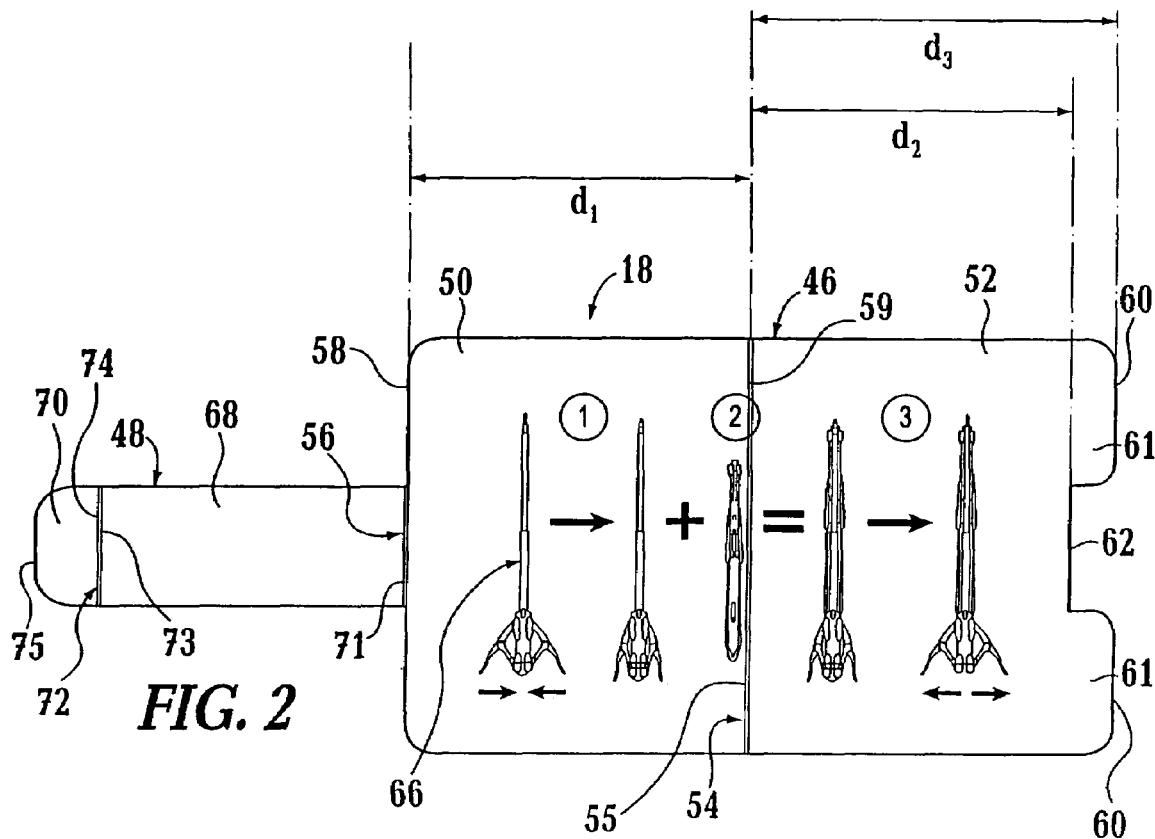
FIG. 2 is a top plan view of the blister card illustrated in FIG. 1.

FIG. 2 shows the blister card 18 in an unfolded state prior to being assembled and placed within the blister tray 10. The blister card 18 includes a main panel 46 and a retaining panel 48 connected thereto. The main panel 46 is subdivided into a front panel 50 and a back panel 52. More particularly, the front panel 50 is connected to the back panel 52 at a first fold line 54 along one edge 55 of the front panel 50, and to the retaining panel 48 at a second fold line 56 along an opposite edge 58 of the front panel 50. As shown in FIG. 2, the front panel 50 may be selected to have an approximate length $d_1$ measured between the opposing edges 55, 58 of the front panel 50.

As illustrated in FIG. 2, the back panel 52 has an edge 59 adjacent the first fold line 54 and an opposite edge 60 defined by a pair of tabs 61 positioned distal to the first fold line 54. The tabs 61 are separated by an opening 62 which has a width that is larger than that of the retaining panel 48 so as to allow the retaining panel 48 to extend between the tabs 61. As described in further detail hereinafter, the tabs 61 are sized and shaped to bias the main panel 46 toward the blister tray 10 after the blister card 18 is inserted therewith. Still referring to FIG. 2, the back panel 52 may be selected to have an approximate length $d_2$ measured between the edge 59 and the opening 62 of the back panel 52, while the back panel 52 may be selected to have an approximate length $d_3$ measured between the opposing edges 59, 60 of the back panel 52. Each of the lengths $d_1$, $d_2$, $d_3$ has a value, such that $d_3 > d_1 > d_2$.

The main panel 46 of the blister card 18 includes graphics and/or indicia 66 printed thereon for aiding and serving as a quick reminder to medical personnel on how to perform one or more common tasks pertaining to the medical devices 12a–c (see FIG. 1) contained in the blister tray 10 (see FIG. 1). For instance, the graphics and/or indicia 66 can include a simplified representation of how the medical devices 12a–c should be assembled. Alternatively, the graphics and/or indicia 66 can include a warning that functions to remind medical personnel on one or more hazards relating to the medical devices 12a–c contained in the blister tray 10.

Still referring to FIG. 2, the retaining panel 48 is subdivided into a long panel 68 and a flap 70. More particularly, the long panel 68 is connected to the front panel 50 at the second fold line 56 along one edge 71 of the long panel 68, and to the flap 70 at a third fold line 72 along an opposite edge 73 of the long panel 68. The retaining panel 48 is sized and shaped to extend between the tabs 61 and through the opening 62 of the back panel 52 when the front panel 50 and the back panel 52 are folded about the first fold line 54, and the retaining panel 48 is folded about the second fold line 56. The flap 70 has an edge 74 adjacent the third fold line 72 and an opposite edge 75 positioned distal to the third fold line 72.

Figure 3:
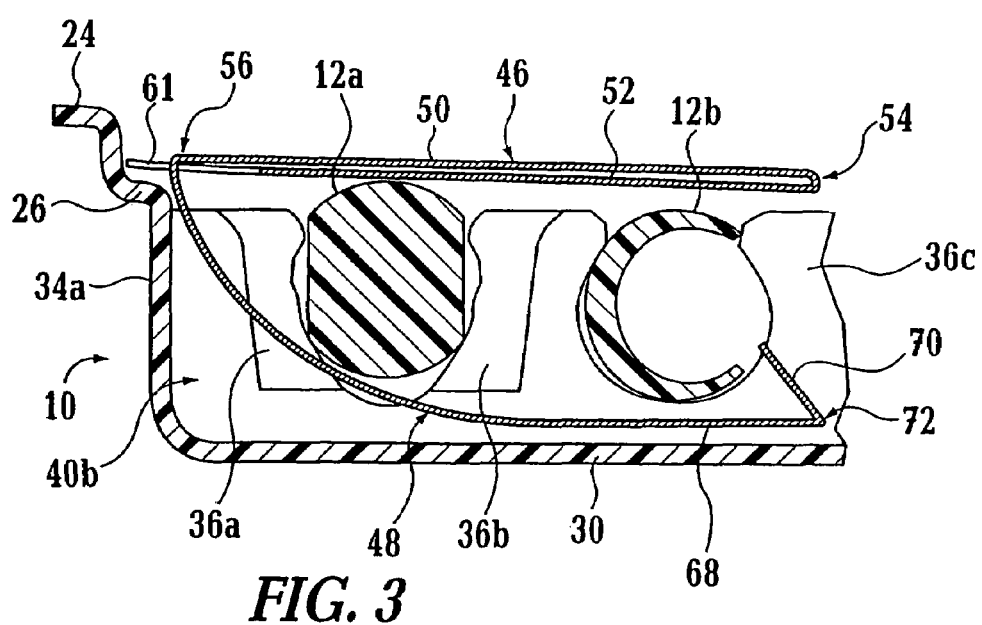
FIG. 3 is a cross-sectional view of the blister tray of FIG. 1, taken along section line 3—3 and looking in the direction of the arrows.

The following description will describe the insertion of the blister card 18 within the blister tray 10 as shown in FIG. 3. Initially, the front panel 50 and the back panel 52 are folded toward each other such that the edge 58 of the front panel 50 abuts a portion of the back panel 52 that is between the opening 62 and the edge 60 of the back panel 52. The front panel 50 and the back panel 52 are folded so as to reduce the length of the blister card 18, thereby reducing space.

Next, the blister card 18 is inserted in the recess 40b within the blister tray 10 by extending the retaining panel 48 between the tabs 61 and through the opening 62 of the back panel 52 and positioning the retaining panel 48 below the medical devices 12a–b such that the flap 70 extends beyond the medical device 12b in a direction away from the longitudinal side 34a of the blister tray 10. The front panel 50 and the back panel 52 are positioned directly above the medical devices 12a–b such that the tabs 61 of the back panel 52 are positioned adjacent the outer peripheral rim 24 and on the inner peripheral ledge 26 of the blister tray 10. In this position, the front panel 50 and the back panel 52 cover a portion of the recess 40b formed in the blister tray 10. The relative position of the front panel 50, the back panel 52, and the medical devices 12a–c is illustrated in FIG. 3. It should be noted that the front panel 50 is positioned directly above the back panel 52. Lastly, the flap 70 of the retaining panel 48 is folded about the third fold line 72.

After the blister card 18 is inserted within the blister tray 10, the tabs 61 of the back panel 52 function to hold the blister card 18 in a planar orientation relative to the blister tray 10, while also biasing the main panel 46 toward the blister tray 10. The tabs 61 also prevent the main panel 46 from pivoting about the second fold line 56 formed between the retaining panel 48 and the front panel 50. The retaining panel 48 functions to hold the blister card 18 in place within the blister tray 10 until the blister card 18 is physically removed therefrom, while also biasing the main panel 46 toward the blister tray 10. Further, the flap 70 functions as an anchor for the blister card 18 so as to hold the blister card 18 firmly in place within the blister tray 10 in instances when the blister tray 10 is accidentally titled or inverted.

Figure 4:
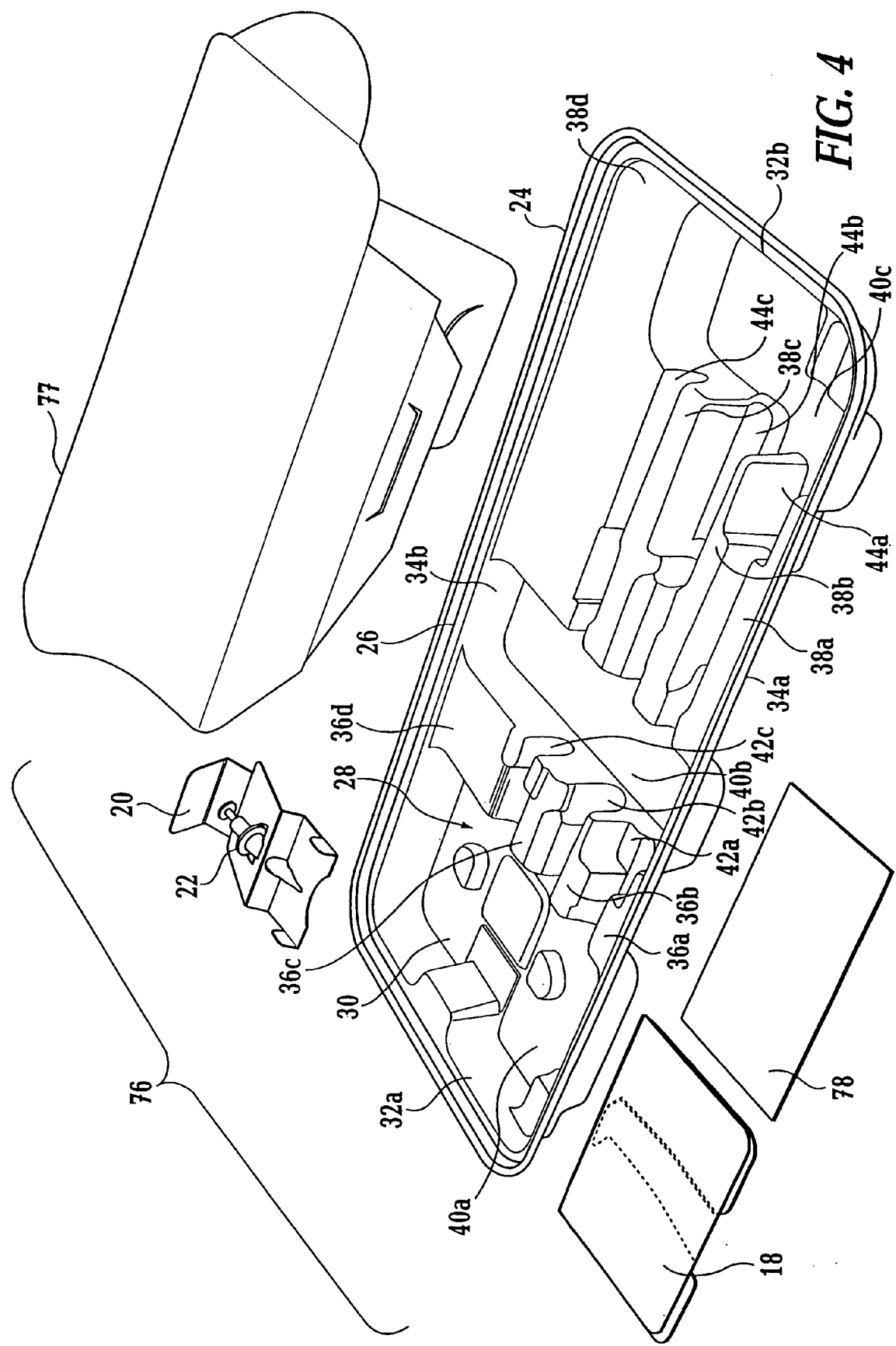
FIG. 4 is an exploded view of the blister tray of FIG. 1, illustrated without medical devices and with a cover.

FIG. 4 shows a kit 76 that includes the blister tray 10 and a cover 77 therefor. To facilitate consideration and discussion, the medical devices 12a–c (see FIG. 1) are not shown in FIG. 4. The kit 76 also includes a kit package 78 (shown schematically) disclosed in commonly owned copending application Ser. No. 10/039,192, now U.S. Pat. No. 6,814,236, entitled, "Kit Package for Multiple Small Devices". The present invention is also related to commonly owned copending application Ser. No. 10/039,172, now U.S. Pat. No. 6,793,078 entitled, "Blister Tray With A Blister Card". Both of these related applications are incorporated herein by reference.

It should be appreciated that the blister card 18 provides numerous advantages. For instance, the blister card 18 can quickly and easily be inserted within the blister tray 10. The blister card 18 is typically made from paper that has sufficient stiffness to hold it in place within the blister tray 10. Alternatively, the blister card 18 can be constructed of any relatively stiff card-like material, including paperboard, plastic, etc. Adhesives or any other locking means are not required to anchor the blister card 18 to the blister tray 10. The blister card 18 does not require any special area, pocket, or locks to hold it in place in the blister tray 10. Also, the blister card 18 does not have to be attached to the blister tray 10.

Figure 5:
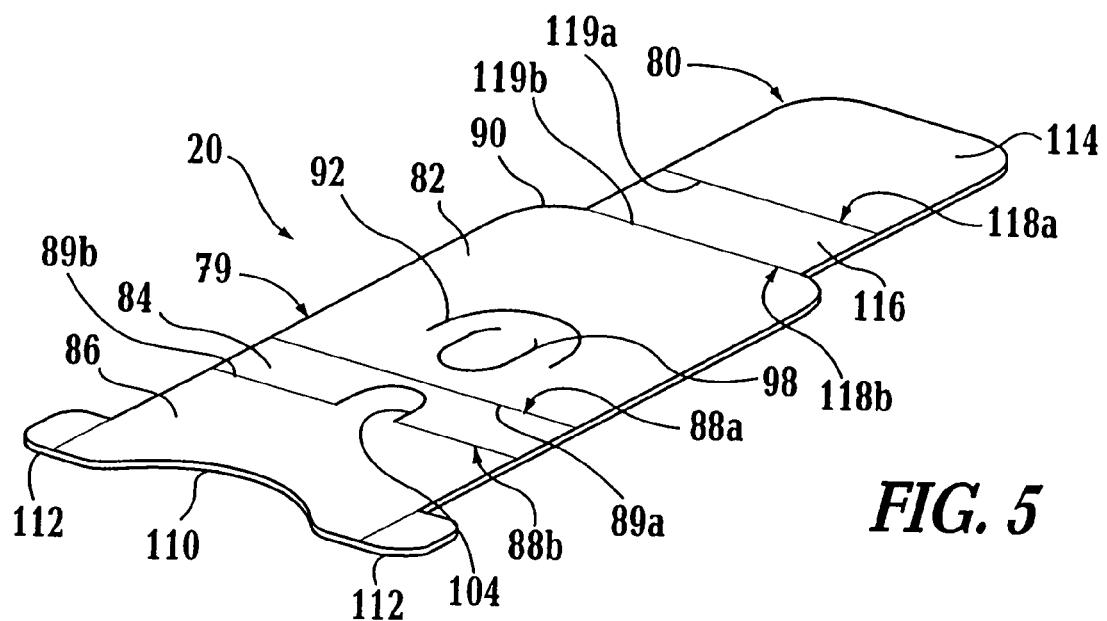
FIG. 5 is a perspective view of a blank used to produce the device package illustrated in FIG. 1.

FIG. 5 shows a blank used to produce the device package 20 in accordance with the present invention. The device package 20 includes a device holding panel 79 and a finger holding area 80 connected thereto. The device holding panel 79 is subdivided into a main section 82, a center section 84, and an anchor section 86. More particularly, the center section 84 is defined by a pair of fold lines 88a–b such that the center section 84 is connected to the main section 82 at the fold line 88a along one edge 89a of the center section 84, and to the anchor section 86 at the fold line 88b along an opposite edge 89b of the center section 84.

Figure 6:
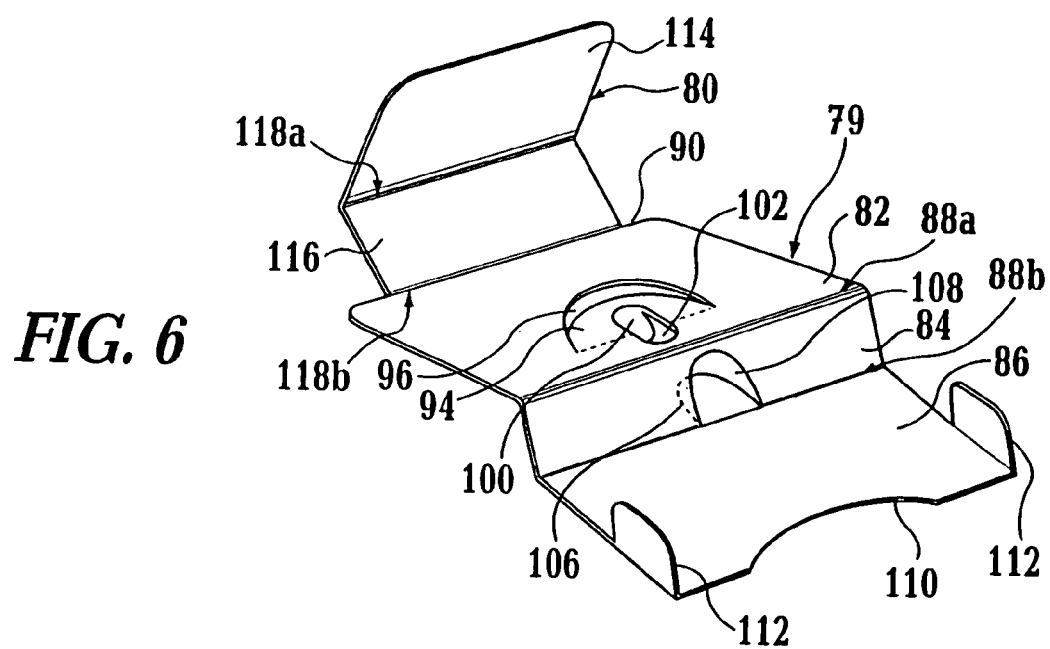
FIG. 6 is a perspective view of the device package assembled from the blank illustrated in FIG. 5, without a medical device.

As illustrated in FIG. 5, the main section 82 is connected to the finger holding area 80 along a distal edge 90 of the main section 82 relative to the fold line 88a. The main section 82 includes a first U-shaped slit 92 that forms an arcuate-shaped flange retaining portion 94 (see FIG. 6) sized and shaped to extend outwardly relative to the main section 82. When the flange retaining portion 94 extends outwardly relative to the main section 82, a first opening 96 (see FIG. 6) is formed in the main section 82. Also, the main section 82 includes a second U-shaped slit 98 that forms a first base 100 (see FIG. 6) sized and shaped to extend outwardly relative to the main section 82. When the first base 100 extends outwardly relative to the main section 82, a second opening 102 (see FIG. 6) is formed in the main section 82. The flange retaining portion 94 is connected to the first base 100 such that the first base 100 is resiliently hinged from the flange retaining portion 94. When the flange retaining portion 94 and the first base 100 extend outwardly relative to the main section 82, the flange retaining portion 94 extends in one direction toward the finger holding area 80, and the first base 100 extends in an opposite direction toward the anchor section 86.

Still referring to FIG. 5, the center section 84 includes a third slit 104 that forms a second base 106 (see FIG. 6) sized and shaped to extend outwardly relative to the center section 84. When the second base 106 extends outwardly relative to the center section 84, a third opening 108 (see FIG. 6) is formed in the center section 84. The second base 106 of the center section 84 is sized and shaped to extend toward the first base 100 of the main section 82.

The anchor section 86 has an inwardly curved distal edge 110 relative to the fold line 88b. The distal edge 110 is inwardly curved so as to reduce the length of the anchor section 86, thereby reducing space. A pair of end flaps 112 is included in the anchor section 86 and is positioned adjacent to the distal edge 110 thereof. The end flaps 112 are sized and shaped to anchor the device package 20 in place within the blister tray 10 (see FIG. 1) as described in further detail hereinafter.

With reference to FIG. 5, the finger holding area 80 is subdivided into a holding tab 114 and a foldable section 116. More particularly, the foldable section 116 is defined by a pair of fold lines 118a–b such that the foldable section 116 is connected to the holding tab 114 at the fold line 118a along one edge 119a of the foldable section 116, and to the main section 82 of the device holding panel 79 at the fold line 118b along an opposite edge 119b of the foldable section 116. The holding tab 114 is sized and shaped so as to allow medical personnel to grasp the device package 20.

Figure 7:
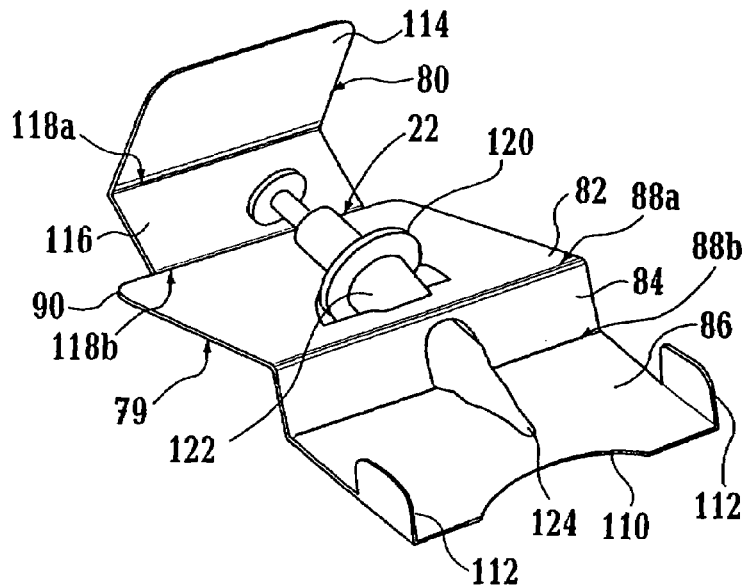
FIG. 7 is a view similar to the view shown in FIG. 6, except that the device package is with a medical device in the form of a vessel inverter.

With reference to FIG. 7, the device package 20 is sized and shaped to hold the small vessel inverter 22. The vessel inverter 22 includes a flange 120, an elongated shaft 122 extending therefrom, and a tip portion 124 extending from the elongated shaft 122.

The following description will describe the insertion of the vessel inverter 22 into the device package 20 and then the insertion of the device package 20 with the vessel inverter 22 within the blister tray 10 as shown in FIGS. 5–8. Initially, the center section 84 of the device holding panel 79 is folded about the fold lines 88a–b such that the center section 84 is at an angle relative to the main section 82 and to the anchor section 86 and such that the main section 82 and the anchor section 86 are extended in opposing directions. Then, the foldable section 116 is folded about the fold lines 118a–b such that the foldable section 116 is at an angle relative to the device holding panel 79 and to the holding tab 114 and such that the holding tab 114 is extended toward the device holding panel 79.

The flange retaining portion 94, the first base 100, and the second base 106 are then extended outwardly such that the first, second, and third openings 96, 102, 108 are formed, respectively. In this position, the first base 100 is adjacent to the second base 106. As illustrated in FIG. 7, the tip portion 124 and the elongated shaft 122 of the vessel inverter 22 are inserted through the second opening 102 such that the elongated shaft 122 of the vessel inverter 22 is retained cooperatively by the first base 100 and the second base 106. The tip portion 124 of the vessel inverter 22 is further inserted through the third opening 108 such that the tip portion 124 of the vessel inverter 22 is positioned on top of the anchor section 86. After the tip portion 124 of the vessel inverter 22 is extended through the third opening 108, the flange 120 of the vessel inverter 22 is retained by the flange retaining portion 94 of the device package 20 so as to lock the vessel inverter 22 therein.

Figure 8:
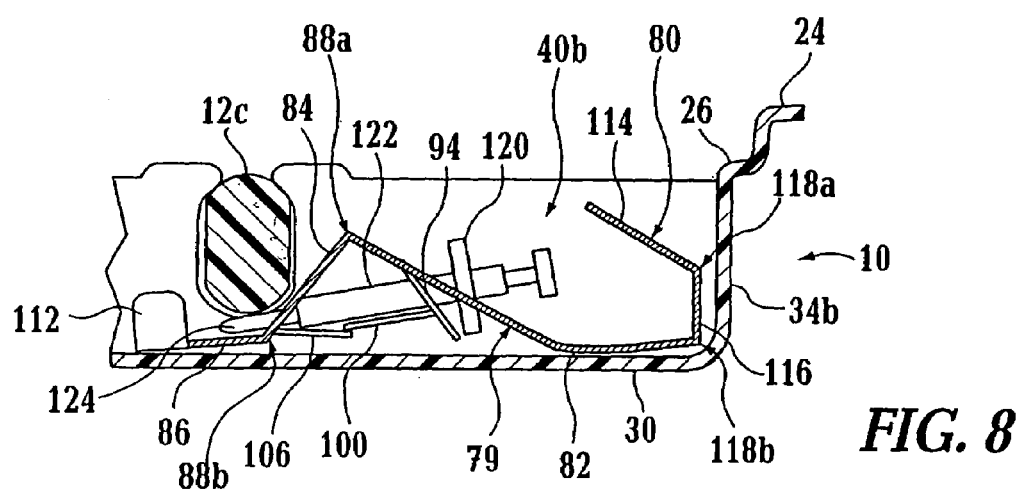
FIG. 8 is a cross-sectional view of the blister tray of FIG. 1, taken along section line 8—8 and looking in the direction of the arrows.

With reference to FIG. 1, the device package 20 is inserted in the recess 40b (see FIG. 4) in the blister tray 10 after the vessel inverter 22 is inserted into the device package 20. As illustrated in FIG. 8, the device package 20 is positioned below the medical device 12c such that the end flaps 112 extend beyond the medical device 12c in a direction away from the longitudinal side 34b of the blister tray 10. In this position, the foldable section 116 of the device package 20 is placed adjacent to the longitudinal side 34b of the blister tray 10. It should be noted that the recess 40b of the blister tray 10 has sufficient space to allow the device package 20 and the blister card 18 to be inserted therein.

After the device package 20 is inserted within the blister tray 10, the end flaps 112 are folded upward. The end flaps 112 allow the medical device 12c to function as an anchor so as to secure the device package 20 firmly in place within the blister tray 10 in instances when the blister tray 10 is accidentally tilted or inverted and when the holding tab 114 is pulled. The end flaps 112 of the device package 20 are sized and shaped to collapse if the device package 20 is pulled out of the blister tray 10 at a sufficient force.

It should be appreciated the above-mentioned steps do not have to occur in the order indicated. For instance, the step of folding the foldable section 116 about the fold lines 118a–b can occur after inserting the device package 20 within the blister tray 10 and after folding the ends flaps 112 of the device package 20 upward.

It should be appreciated that the device package 20 provides numerous advantages. For instance, the device package 20 can hold the vessel inverter 22 to be incorporated into the formed blister tray 10, can be easily assembled, and can be easily arranged within the formed blister tray 10. As is evident from the description above, the device package 20 can be inserted into the existing recess 40b in the blister tray 10 so as to allow an additional medical device (e.g., the vessel inverter 22) to be inserted into the blister tray 10. The vessel inverter 22 can be removed from the device package 20 regardless of whether the device package 20 is anchored in the blister tray 10 and before the medical devices 12a–c are deployed. The device package 20 is configured such that when it is folded about the fold line 88a, the vessel inverter 22 can be quickly inserted into the openings 96, 102, 108 and such that when the device package 20 is straighten, it locks the vessel inverter 22 in place. The folds and the curve of the device package 20 act as a spring to anchor and hold the vessel inverter 22 in place. The device package 20 is typically made from paper that has sufficient stiffness to hold the vessel inverter 22 in place therein. Alternatively, the device package 20 can be constructed of any relatively stiff material, including paperboard, etc. Adhesives or other locking means are not required to anchor the device package 20 within the blister tray 10. Cut-out areas, which require paper removal and which have correspondingly high manufacturing costs, are not required in the device package 20. Also, the device package 20 does not have to be attached to the blister tray 10.

Figure 9:
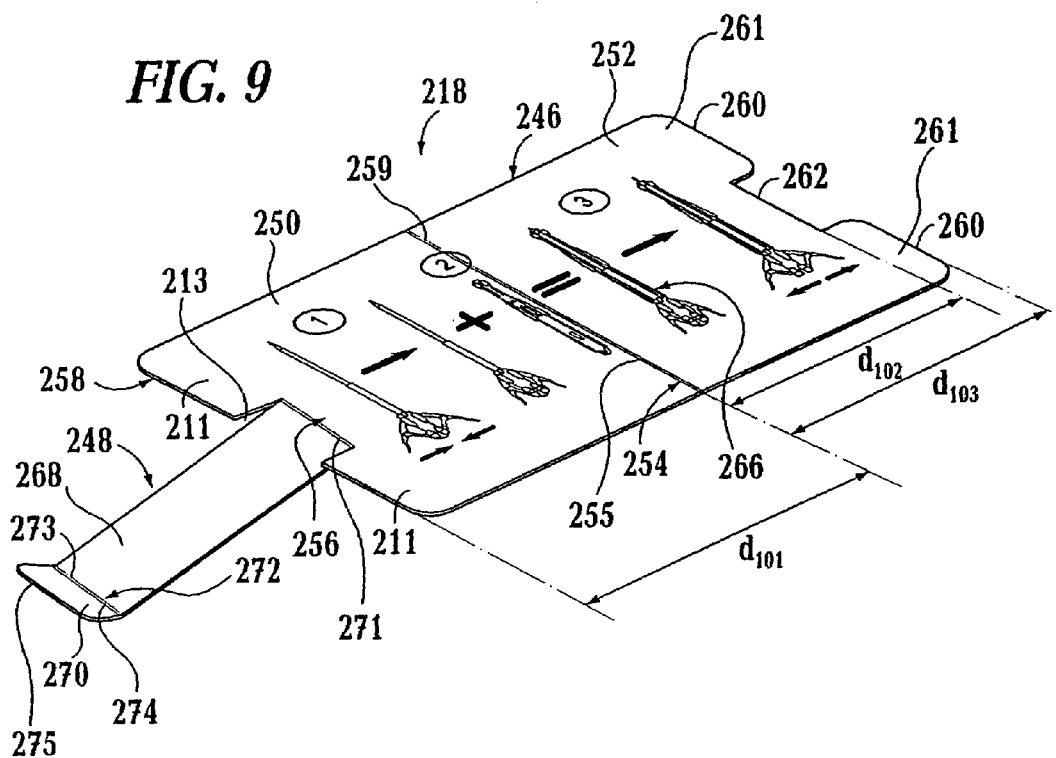
FIG. 9 is a perspective view of a blister card constructed in accordance with another exemplary embodiment of the present invention.
Figure 11:
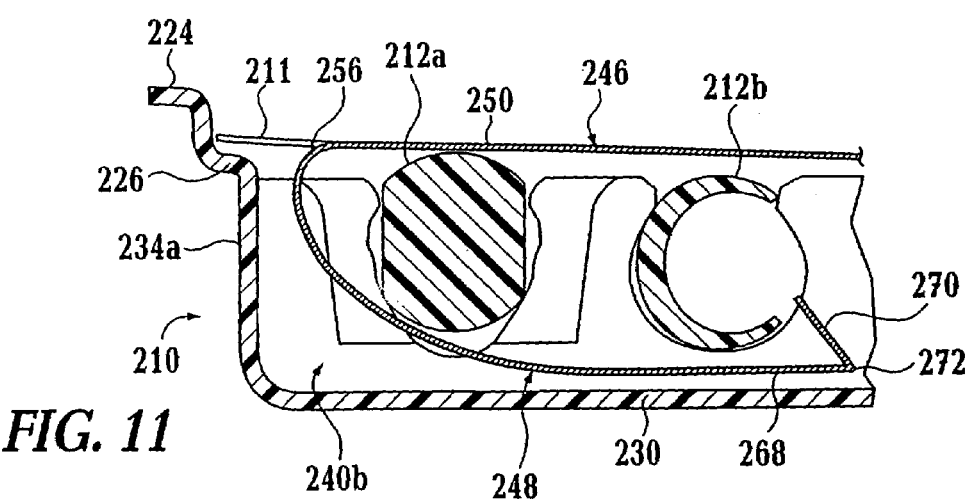
FIG. 11 is a cross-sectional view of the blister tray of FIG. 10, taken along section line 10—10 and looking in the direction of the arrows.
Figure 10:
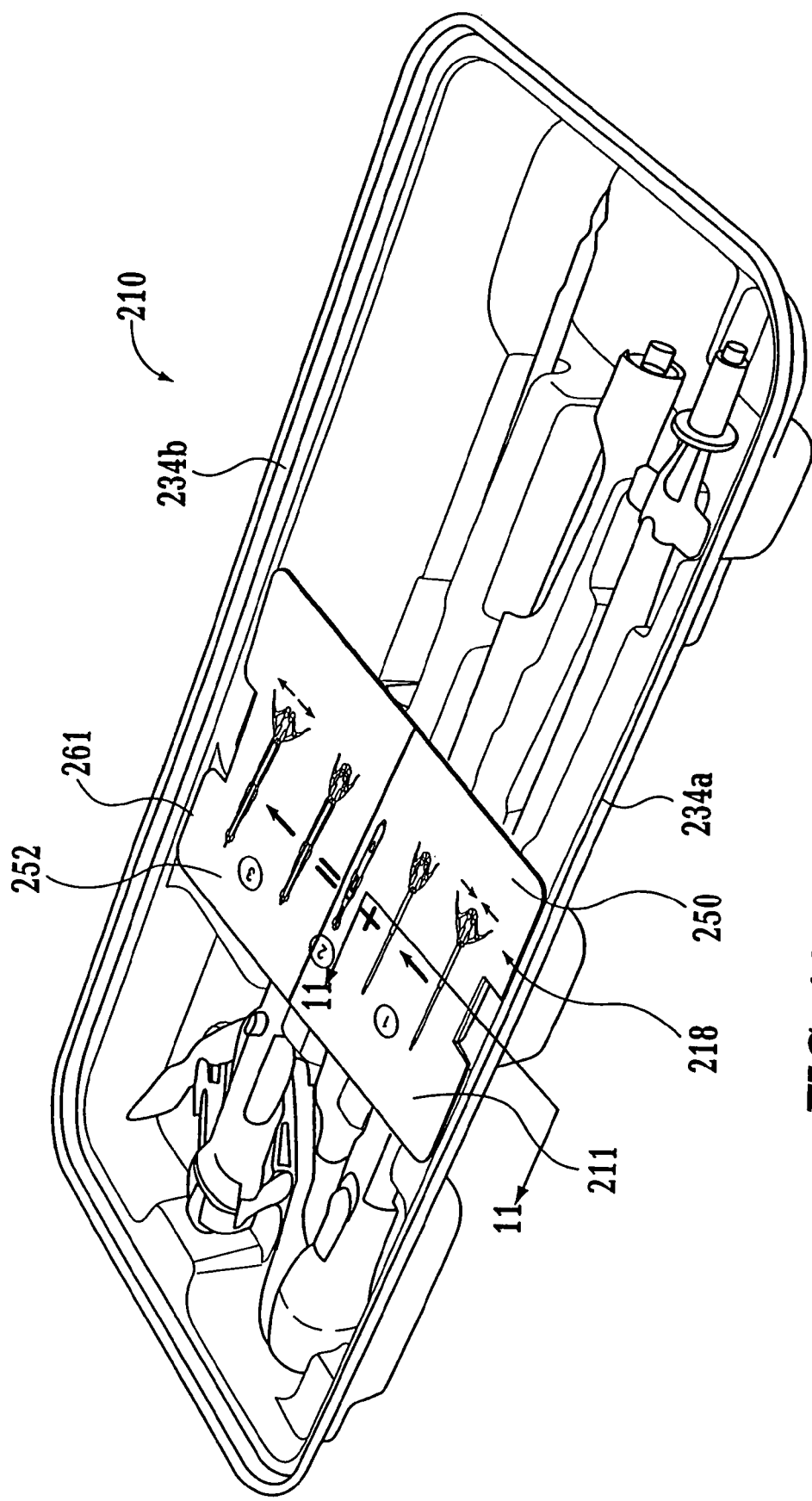
FIG. 10 is a perspective view of a blister tray, shown with the blister card of FIG. 9.

Another exemplary embodiment of the blister tray 10 (see FIG. 2) is illustrated in FIGS. 9–11. Elements illustrated in FIGS. 9–11 which correspond to the elements described above with reference to FIGS. 1–4 have been designated by corresponding reference numerals increased by two hundred. In addition, elements illustrated in FIGS. 9–11 which do not correspond to the elements described above with reference to FIGS. 1–4 have been designated by odd numbered reference numerals starting with reference number 211. The embodiment of FIGS. 9–11 operates in the same manner and provides the same advantages as the embodiment of FIGS. 1–4, unless it is otherwise stated.

FIG. 9 shows a blister card 218 prior to being inserted within a blister tray 210 (see FIG. 10). It will be understood that the blister tray 210 is identical to the blister tray 10 illustrated in FIG. 1. The blister card 218 includes a main panel 246 and a retaining panel 248 connected thereto. The main panel 246 is subdivided into a front panel 250 and a back panel 252. More particularly, the front panel 250 is connected to the back panel 252 at a first fold line 254 along one edge 255 of the front panel 250, and to the retaining panel 248 at a second fold line 256 along an opposite edge 258 of the front panel 250. Although the front panel 250 and the back panel 252 are connected by the first fold line 254, the front panel 250 and the back panel 252 are not folded about the first fold line 254 when the blister card 218 is inserted within the blister tray 210 as explained in further detail hereinafter. As shown in FIG. 9, the front panel 250 may be selected to have an approximate length $d_{101}$ measured between the opposing edges 255, 258 of the front panel 250.

Unlike the front panel 50 (see FIG. 2) described above, the front panel 250 includes a pair of tabs 211 positioned distal to the first fold line 254. The retaining panel 248 is positioned between the tabs 211 and is sized and shaped to pivot about the second fold line 256. When the retaining panel 248 pivots about the second fold line 256, an opening 213 is formed between the tabs 211 of the front panel 250. As described in further detail hereinafter, the tabs 211 of the front panel 250 are sized and shaped to bias the main panel 246 toward the blister tray 210 after the blister card 218 is inserted therewith.

As illustrated in FIG. 9, the back panel 252 has an edge 259 adjacent the first fold line 254 and an opposite edge 260 defined by a pair of tabs 261 positioned distal to the first fold line 254. The tabs 261 of the back panel 252 are separated by an opening 262. As described in further detail hereinafter, the tabs 261 of the back panel 252 are sized and shaped to bias the main panel 246 toward the blister tray 210 after the blister card 218 is inserted therewith. Still referring to FIG. 9, the back panel 252 may be selected to have an approximate length $d_{102}$ measured between the edge 259 and the opening 262 of the back panel 252, while the back panel 252 may be selected to have an approximate length $d_{103}$ measured between the opposing edges 259, 260 of the back panel 252. Each of the lengths $d_{101}$, $d_{102}$, $d_{103}$ has a value, such that $d_{101} > d_{103} > d_{102}$.

Like the main panel 46 (see FIG. 2), the main panel 246 also includes graphics and/or indicia 266 printed thereon for aiding and serving as a quick reminder to medical personnel on how to perform one or more common tasks pertaining to medical devices 212a–c contained in the blister tray 210.

Still referring to FIG. 9, the retaining panel 248 is subdivided into a long panel 268 and a flap 270. More particularly, the long panel 268 is connected to the front panel 250 at the second fold line 256 along one edge 271 of the long panel 268, and to the flap 270 at a third fold line 272 along an opposite edge 273 of the long panel 268. The flap 270 has an edge 274 adjacent the third fold line 272 and an opposite edge 275 positioned distal to the third fold line 272.

The main panel 246 of the blister card 218 has a length, measured between the tabs 261 of the back panel 252 and the tabs 211 of the front panel 250, which approximates the width of the blister tray 210 measured between longitudinal sides 234a–b of the blister tray 210.

The following description will describe the insertion of the blister card 218 within the blister tray 210 as illustrated in FIG. 11. Initially, the blister card 218 is inserted within the blister tray 210 by folding the retaining panel 248 about the second fold line 256 and positioning the retaining panel 248 below the medical devices 212a–b such that the flap 270 extends beyond the medical device 212b. The front panel 250 and the back panel 252 are positioned directly above the medical devices 212a–c such that the tabs 211 of the front panel 250 and the tabs 261 of the back panel 252 are positioned adjacent the opposing longitudinal sides 234a–b of the outer peripheral rim 224 and on the inner peripheral ledge 226 of the blister tray 210. In this position, the main panel 246 covers a recess 240b formed in the blister tray 210. As illustrated in FIG. 11, the front panel 250 and the back panel 252 are not folded about the first fold line 254.

After the blister card 218 is inserted within the blister tray 210, the tabs 211 of the front panel 250 and the tabs 261 of the back panel 252 function to hold the blister card 218 in a planar orientation relative to the blister tray 210, while also biasing the main panel 246 toward the blister tray 210 without folding. The main panel 246 functions to bias the front panel 250 and the back panel 252 toward the blister tray 210.

It should be noted that the present invention can have numerous modifications and variations. For instance, while the present invention has been described herein in conjunction with the blister tray 10, 210, the blister card 18, 218 and the device package 20 can be used in connection with other blister trays. Also, while the device package 20 has been described herein to hold the vessel inverter 22, the device package 20 can hold other types of medical devices.

It will be understood that the embodiment described herein is merely exemplary and that a person skilled in the art may make many variations and modifications without departing from the spirit and scope of the invention. All such variations and modifications, including those discussed above, are intended to be included within the scope of the invention as defined in the appended claims.

The invention claimed is:

1. A package made from a planar sheet, comprising:
a first foldable panel including a first fold line and a second fold line positioned on one side of said first fold line, a main section positioned on an opposite side of said first fold line, and a center section positioned between said first fold line and said second fold line, said main section having a first slit that forms a retaining portion moveable such that said retaining portion extends outwardly from said main section so as to create a first opening in said first panel, and a second slit that forms a first base moveable such that said first base extends outwardly from one side of said first panel so as to create a second opening therein, said center section having a third slit that forms a second base moveable such that said second base extends outwardly from said one side of said first panel so as to create a third opening therein, said first opening and said second opening being aligned with each other when said first panel is folded about said first fold line such that said first base is adjacent to said second base, and said third opening cooperating with said first and second openings, when they are aligned with each other, to form a receptacle for a medical device.

2. The package of claim 1, wherein said first foldable panel further includes an anchor section adjacent to said center section, said anchor section including a pair of end flaps engageable with a medical device contained in a blister tray.

3. The package of claim 2, further comprising a second foldable panel connected to said first foldable panel, said second foldable panel including a third fold line and a fourth fold line positioned on one side of said third fold line, a holding tab positioned on an opposite side of said third fold line, and a sub-panel positioned between said third fold line and said fourth fold line.

4. The package of claim 3, wherein said first foldable panel has a first width and said second foldable panel has a second width, said first width being larger than said second width.

5. The package of claim 4, wherein said anchor section includes an inwardly curved distal edge.

* * * * *